United States Patent [19]

Hiraga et al.

[11] 4,228,241
[45] Oct. 14, 1980

[54] METHOD FOR PRODUCING A PEPTIDASE

[75] Inventors: Hirofumi Hiraga, Kanagawa; Ryuichi Miyajima; Koji Mitsugi, both of Yokohama, all of Japan

[73] Assignee: Ajinomoto Company, Incorporated, Tokyo, Japan

[21] Appl. No.: 889,877

[22] Filed: Mar. 24, 1978

[30] Foreign Application Priority Data

Mar. 28, 1977 [JP] Japan ................... 52-34295

[51] Int. Cl.² ............................... C12N 9/48
[52] U.S. Cl. ................... 435/212; 435/225; 435/913; 435/918
[58] Field of Search ............. 195/65, 66 R, 62, 114, 195/53, 55; 435/212, 219-226

[56] References Cited

U.S. PATENT DOCUMENTS

| 2,888,385 | 5/1959 | Grandel | 195/67 |
| 3,361,643 | 1/1968 | Fukushima et al. | 195/66 R |
| 3,645,850 | 2/1972 | Ichishima et al. | 195/66 R |
| 3,947,323 | 3/1976 | Young | 195/65 |
| 3,957,581 | 5/1976 | Tobe et al. | 195/65 |

FOREIGN PATENT DOCUMENTS

| 50-46891 | 4/1975 | Japan | 195/65 |
| 50-88283 | 7/1975 | Japan | 195/65 |

*Primary Examiner*—Lionel M. Shapiro
*Attorney, Agent, or Firm*—Oblon, Fisher, Spivak, McClelland & Maier

[57] ABSTRACT

A method is provided for producing a peptidase capable of substantially completely hydrolyzing protein into its constituent amino acids which comprises culturing a strain of filamentous fungus, belonging to one of the species *Aspergillus oryzae* and *Aspergillus soyae* and characterized in that said strain is capable of producing said peptidase, in a nutrient culture medium containing at least one substrate selected from the group consisting of a fatty acid having 14, 16, 18 or 20 carbon atoms and a derivative of said fatty acid, and recovering said peptidase from said culture medium. It is particularly effective to use a combination of a sugar ester of a fatty acid and a vegetable oil as substrates in a liquid culture medium.

9 Claims, 1 Drawing Figure

METHOD FOR PRODUCING A PEPTIDASE

BACKGROUND OF THE INVENTION

1. Field of the Invention

This invention relates to a method for producing a remarkably efficient peptidase using a koji (yeast) mold. More particularly, it is concerned with a method which comprises culturing a koji mold in a nutrient culture medium containing one or more fatty acids having 14, 16, 18, or 20 carbon atoms, their derivatives, or a vegetable oil containing these fatty acids, and recovering the accumulated peptidase from the culture medium.

2. Discussion of the Prior Art

Koji mold has been utilized in Japan for centuries in brewing shoyu (Japanese soy sauce), Japanese sake, or bean paste, and it is well known that peptidase enzymes produced by these koji molds play a central role in these brewing processes. One of the most serious problems of shoyu brewing is that it is a time-consuming process; usually it takes 6 to 12 months.

On the other hand, a chemical soy sauce has been manufactured by a process which includes an acid-catalyzed hydrolysis of defatted soybeans. This process was carried out under intensive conditions using a large amount of conc. hydrochloric acid at a high temperature (100°–120° C.) for more than 6 hours. However, in the acid-catalyzed hydrolysis process, although the hydrolysis ratio of defatted soybean is extremely high and the soybean is hydrolyzed completely, the chemical soy sauce so obtained is inferior to brewed shoyu in quality. Besides, useful substances unstable to acid hydrolysis such as tryptophan and carbohydrates contained in defatted soybean are decomposed to form undesirable substances such as disagreeable organic acids and colored material.

Recently, an enzyme-catalyzed hydrolysis process (enzyme process) has been tried to manufacture a shoyu within as short a time as 2 to 4 weeks. This process comprises hydrolyzing a defatted soybean with enzymes obtainable from koji mold, and attempting to impart to the resultant hydrolyzate a preferable shoyu-like flavor by lactic and yeast fermentations. However, it is pointed out that the shoyu-like seasoning obtained by the modified enzyme process is inferior to shoyu in taste, as well as flavor, because of a low hydrolysis ratio of protein to amino acids, and especially because of a low liberating ratio of glutamic acid.

Although an enzyme-catalyzed hydrolysis of pure proteins such as milk casein or fibroin might be expected to produce an aqueous solution of amino acids suitable for medical or nutritional use, the production of such an aqueous solution of amino acids has never been adequately realized. One of the reasons heretofore preventing the practical use of such hydrolyzates undoubtedly resides in the fact that the extent of protein hydrolysis is insufficient. To be useful for this purpose, a protein has to be hydrolyzed to its constituent amino acids as completely as it is in an acid-catalyzed hydrolysis process.

A need therefore continues to exist for a method of producing an efficient peptidase preparation which is capable of hydrolyzing protein almost completely to its constituent amino acids.

SUMMARY OF THE INVENTION

Accordingly, one object of the present invention is to provide a new method for producing an efficient peptidase capable of hydrolyzing protein almost completely to its constituent amino acids.

Briefly, this object and other objects of the invention as hereinafter will become more readily apparent can be attained by providing a method for producing a peptidase capable of substantially completely hydrolyzing protein into its constituent amino acids which comprises culturing a strain of filamentous fungus, belonging to one of the species Aspergillus oryzae and Aspergillus sojae and characterized in that said strain is capable of producing said peptidase, in a nutrient culture medium containing at least one substrate selected from the group consisting of a fatty acid having 14, 16, 18 or 20 carbon atoms and a derivative of said fatty acid, and recovering said peptidase from said culture medium.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein.

DETAILED DESCRIPTION OF THE PREFERRED EMBODIMENTS

Figure 1:
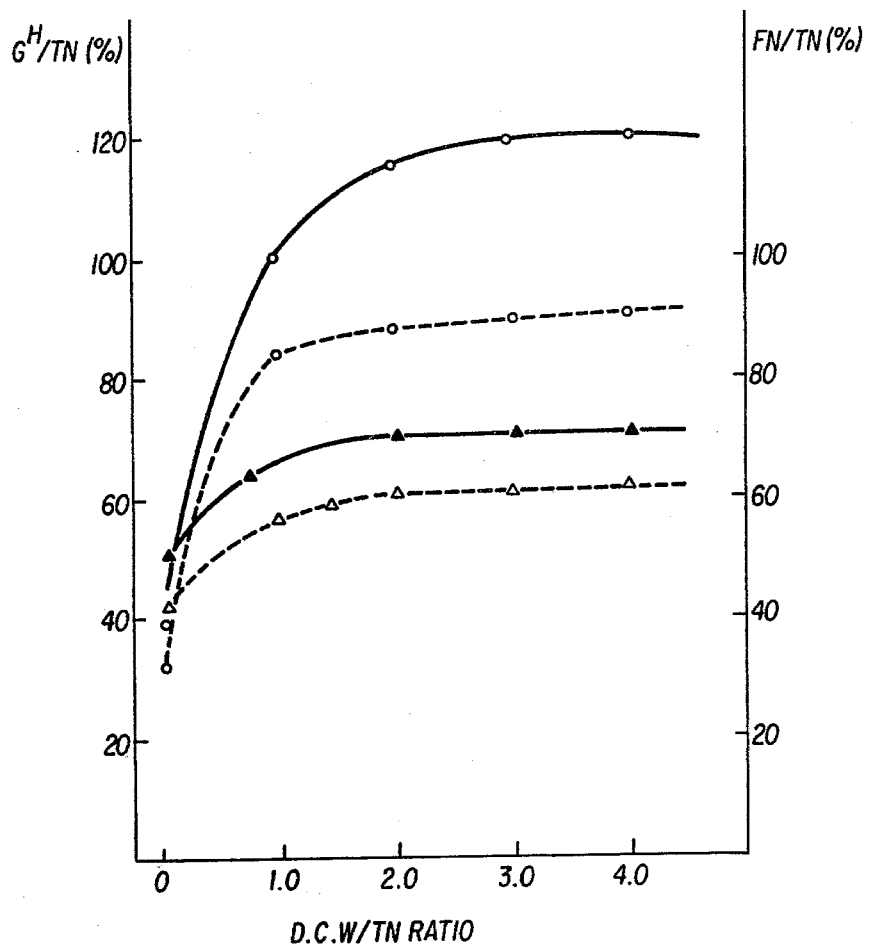
FIG. 1 is a plot of formol nitrogen as a percentage of total nitrogen and liberated glutamic acid as a percentage of total nitrogen vs. the ratio of dry cell weight to total nitrogen.

The method of the present invention comprises culturing a koji mold in a nutrient culture medium containing one or more fatty acids having 14, 16, 18, or 20 carbon atoms, their derivatives, or vegetable oils containing these fatty acids, and recovering an accumulated peptidase from the culture medium.

The koji molds employed according to the present invention are fungi belonging to the species *Aspergillus oryzae* and *Aspergillus soyae* (synonym of *Aspergillus parasiticus*), which are easily available from a commercial mold starter sold in Japan.

According to a preferred embodiment of the present invention, a strain which is capable of producing a stronger peptidase than any other strain tested is selected from among those obtainable from commercially available mold starters sold in Japan.

In general, microbial cells of these koji mold will conglomerate to form thick curds when cultured in a liquid medium. This is not desirable for enzyme production.

Therefore, it is preferable to select a strain which will form microbial pellets in liquid culture, in addition to its excellent ability to produce a stronger peptidase. Such strains can easily be produced by a conventional single cell colony isolation process from a commercial mold starter (Japanese Shoyu Koji).

For example, Aspergillus oryzae FERM-P 4149 (NRRL 11274) was selected and isolated from a commercial mold starter manufactured and sold by Nihon Jozo Cogyo Co., Ltd. by the usual single colony isolation techniques.

The strain identified by the above FERM-P and NRRL numbers has been deposited with, and is available from, the Fermentation Research Institute of the Agency of Industrial Science and Technology, Chiba-shi Chiba-ken, Japan, and Northern Utilization Research and Development Division, U.S. Department of Agriculture, Peoria, Illinois.

In a more preferred embodiment of the present invention, an artificial mutant which may produce a stronger peptidase is easily induced by conventional mutation processes such as UV or X-ray irradiation, or NG treatment.

The nutrient medium employed in the process of the present invention may be any conventional medium used for production of proteolytic enzymes, and would typically contain a carbon source, a nitrogen source such as $NH_4NO_3$, $(NH_4)_2SO_4$, urea, soybean, wheat bran, and peptone, and inorganic ions such as $K^+$, $Na^+$, $Ca^{2+}$, $Mg^{2+}$, $Mn^{2+}$, $Zn^{2+}$, $Fe^{2+}$, $SO_4^{2-}$, $PO_4^{3-}$.

According to a preferred embodiment of the present invention, a liquid culture medium containing 0.5 to 1.5% of wheat bran and 0.5 to 1.5% of defatted soybean is employed.

The peptidase activity is increased to some extent in proportion to the concentration of these substrates, but no further increase in the activity is observed when the nutrient medium contains more than 4% of these substrates since the culture broth becomes thick and mushy, which is not suitable for enzyme production.

For the peptidase production, it is not effective to add carbohydrates such as glucose, sucrose, starch, or molasses to these media. Carbohydrates are effective only to increase the quantity of mycelia of the fungus as much as 2 to 3 times, but no further increase in peptidase activity is produced thereby.

According to the present invention, wheat or a mixture of wheat and wheat bran is used as an excellent solid medium.

Suitable substrates for the nutrient medium which accelerate enzyme production include the following fatty acids having 14, 16, 18 and 20 carbon atoms, their derivatives, and vegetable oils containing these fatty acids.

(1) Fatty acids:
  myristic acid ($C_{14}$), palmitic acid ($C_{16}$), stearic acid ($C_{18}$),
  oleic acid ($C_{18}$), linoleic acid ($C_{18}$), arachidic acid ($C_{20}$).

(2) Sugar esters:
  sucrose monomyristate, sucrose monopalmitate, sucrose monooleate, sucrose monostearate, sucrose distearate.

(3) Sorbitan esters:
  sorbitan monopalmitate, sorbitan monooleate, sorbitan monostearate.

(4) Polyoxyethylene sorbitan monopalmitate:

(5) Phospholipids of the above fatty acids:
  phosphatidyl ethanolamine

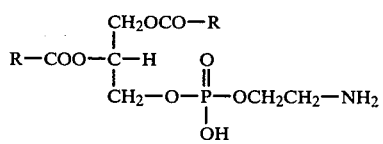

phosphatidyl choline (lecithin)

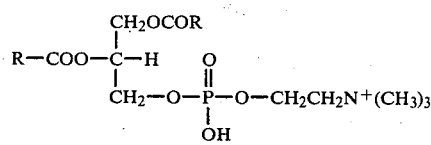

egg lecithin, soybean lecithin (6) Mono, di, and triglyceride esters of the above fatty acids: glycerine monostearate.

(7) Vegetable oils containing the above fatty acids in the form of free acid, or triglycerides as their components:
  soybean oil, corn oil, coconut oil, safflower oil (high oleic oil), rice bran oil, rapeseed oil, olive oil, cotton seed oil, kapok oil, sesame oil.

According to the present invention, one or more of these additives are added to the nutrient medium, in an amount of 0.5 to 4.0% by weight. Among these additives, sugar esters of fatty acids are especially effective for making the mycelia of the koji mold form microbial fine beads ($50 \sim 500\mu$) in liquid culture. This is generally preferable for enzymes production, since the liquid culture of a koji mold can be carried out far more readily, and peptidase activity is increased as well, when microbial mycelia form microbial fine beads.

Therefore, according to a preferred embodiment of the present invention, almost equal quantities of a sugar ester and a vegetable oil (0.5 to 1.5%) are added to the nutrient medium.

According to the present invention, a koji mold is cultured aerobically in a liquid culture medium containing these additives at a temperature ranging from 20° C. to 40° C., at a pH ranging from 3.5 to 8.5 for 2 to 10 days.

Alternatively, a koji mold is cultured in a solid culture medium such as wheat bran or a mixture of wheat bran-defatted soybean in a similar manner to the koji process in Japan.

The enzyme preparation referred to as a peptidase in the present invention is a series of peptidases obtainable from a koji mold, which may hydrolyze various kind of peptides, and proteins to their constituent amino acids, with or without the aid of proteolytic enzymes such as pepsin, trypsin, and other microbial proteases.

In other words, the peptidase of the present invention is a mixture of peptidases obtainable from koji mold such as various kinds of leucineamino peptidases (LAPase), carboxypeptidases (CPase), oligopeptidases, dipeptidases, $\alpha$-glutamylaminopeptidase ($\alpha$-GAPase), glutaminase, peptidoglutaminase and glutamic acid-liberating peptidases.

The peptidase of the present invention accumulates mostly in fine microbial beads (cells) when cultured in liquid culture. The microbial fine beads of the peptidase, when separated from the culture broth, represent a convenient form in that they can be used in a manner analogous to immobilized enzymes.

If the process of the present invention is carried out in solid culture, the peptidase accumulates in the solid culture medium and is easily extracted from the solid culture medium with water or buffer solutions, and then recovered from the crude extract by a conventional method. The crude enzyme may be prepared precipitating the enzymes by addition of inorganic salts such as ammonium sulfate, sodium sulfate or chilled organic solvent such a acetone, isopropanol, or ethanol, and by recovering the precipitated enzyme.

The activity of the peptidase of the present invention is assayed as total peptidase activity to purified soybean proteins partially hydrolyzed by protease, and is measured by the following method:

14 ml of 5% Ajipron $S_2$ (purified soybean protein, with a content of 85% protein, manufactured by Ajinomoto Co., Inc.) solution whose pH is adjusted to 7.0 is introduced into a 100 ml Erlenmeyer flask with cotton plug, and heated at 120° C. for 15 minutes for sterilization. To this substrate solution, 6.0 g of a culture broth of the koji mold (or 6.0 ml of enzyme solution) is added, and the mixture is allowed to stand at 40° C. for 5 days with occasional stirring by shaking. After 5 days enzymation, the flask and contents are heated at 100° C. for 100 minutes, then, clear filtrate is obtained by gravity filtration of the reaction mixture with No. 5B filter paper. For each sample, the concentrations of total nitrogen (TN), formol nitrogen (FN), and liberated glutamic acid ($G^H$) are determined by the Kjeldahl method, the formol titration method, and the glutamic acid dehydrogenase method, respectively.

The peptidase activity is measured by both the FN/TN and $G^H$/TN (liberation ratio of glutamic acid) ratios in percentages.

In addition to the total peptidase activity mentioned above, each peptidase activity is of course determined by the conventional methods. The peptidase activity of every enzyme produced according to the present invention is increased by as much as about 2 to 6 times, compared with the activity of those produced by a conventional process.

For example, glutaminase, LAPase, and α-GAPase activities are increased by as much as 4 to 6, 4 to 5, and 2 to 3 times, respectively.

Since each individual peptidase activity of the peptidase preparation is significantly increased, the total peptidase activity is also increased. Especially, the peptidase activity of the enzyme obtainable by culturing a koji mold in a liquid culture medium containing both a vegetable oil and a sugar ester of a fatty acid is powerful enough to hydrolyze various kinds of proteins to their constituent amino acids as completely as an acid-catalyzed hydrolysis process.

By using the peptidase of the present invention, an amino acid seasoning comparable to shoyu can be manufactured by subjecting the hydrolyzate prepared by the enzyme-catalyzed hydrolysis of defatted soybean to a series of flavor-vesting fermentations such as lactic and yeast fermentation. Furthermore, a purified aqueous solution of amino acids obtainable by using the peptidase of the present invention is available for medical or nutritional use.

Having generally described the invention, a more complete understanding can be obtained by reference to certain specific examples, which are included for purposes of illustration only and are not intended to be limiting unless otherwise specified.

EXAMPLE 1

To 150 g wheat bran (manufactured by Nisshin Flour Milling Co., Ltd. Tokyo), 5.0 l water and 4.0 ml of 30% NaOH were added, and the mixture was heated at 85° C. for 1.0 hour. After the extraction, 4.0 l of wheat bran extract was obtained by filtering the extracted mixture with filter paper.

Then, a basal liquid medium containing the wheat bran extract shown in Table 1 was prepared.

TABLE 1

| Basal Liquid Medium | |
|---|---|
| Components | Amount |
| wheat bran extract | 25 ml |
| Ajipron $E_2$* | 0.75 g |
| $KH_2PO_4$ | 0.25 g |
| water | 25 ml |

*with content of 60% crude protein

To 50 ml of the basal medium, either a fatty acid, its derivative, or a vegetable oil containing the fatty acid as shown in Tables 2 and 3 was added, and the pH of each liquid medium was adjusted to 6.0.

Then, each liquid medium was put into a 500 ml shaking flask, and heated at 120° C. for 15 minutes for sterilization.

Separately, 20 strains of Aspergillus oryzae whose mycelia formed microbial pellets when cultered in liquid culture were selected from among 100 strains isolated from the commercial mold starter (manufactured by, and available from, Nihon Jozo Kogyo Co., Ltd.). Among these 20 strains, *Aspergillus oryzae* No. 142 (FERM-P 4149) was selected, whose ability to produce peptidase is stronger than any other strain.

The No. 142 strain was cultured on potato-dextrose agar slants (pH 6.0) at 30° C. for 3 days, inoculated into the liquid medium previously prepared, and cultured at 31° C. for 2 days with shaking (shaking width, 7.0 cm, 115 oscil./min.). For each sample, the total peptidase activity to pure soybean protein of the culture broth was determined using the assay previously described, and the results obtained are shown in Tables 2 and 3.

TABLE 2

Effects of fatty acids and their derivatives on the production of the peptidase

| | | Peptidase activity | |
|---|---|---|---|
| Fatty acid and its derivatives | Amount added to the medium (%) | FN/TN (%) | $G^H$/TN (%) |
| none | — | 55.0 | 59.0 |
| (1) free fatty acid: | | | |
| lauric acid ($C_{12}$) | 1.5 | 10.0 | 20.0 |
| myristic acid ($C_{14}$) | 1.0 | 62.2 | 82.1 |
| palmitic acid ($C_{16}$) | 1.5 | 61.9 | 81.7 |
| stearic acid ($C_{18}$) | " | 61.4 | 79.5 |
| oleic acid ($C_{18}$) | " | 58.3 | 75.8 |
| linoleic acid ($C_{18}$) | " | 58.0 | 72.2 |
| arachidic acid ($C_{20}$) | 1.0 | 62.6 | 73.6 |
| (2) sugar ester: | | | |
| sucrose monopalmitate | 1.0 | 60.7 | 72.2 |
| sucrose distearate | 1.0 | 60.8 | 82.1 |
| (3) sorbitan ester: | | | |
| sorbitan monopalmitate | 1.0 | 62.1 | 77.9 |
| (4) polyoxyethylene sorbitan monopalmitate | 1.0 | 61.5 | 75.0 |
| (5) phospholipid: | | | |
| egg lecithin | 3.0 | 60.2 | 82.6 |
| phosphatidyl choline | 1.0 | 58.0 | 65.8 |
| phosphatidyl ethanolamine | 1.0 | 57.5 | 64.8 |

TABLE 3

Effects of vegetable oils on production of the peptidase

| | | peptidase activity | |
|---|---|---|---|
| vegetable oil | (main fatty acid) | FN/TN (%) | $G^H$/TN (%) |
| soybean oil | (palmitate, stearate) | 60.9 | 77.8 |

TABLE 3-continued

Effects of vegetable oils on production of the peptidase

| vegetable oil | (main fatty acid) | peptidase activity FN/TN (%) | $G^H$/TN (%) |
|---|---|---|---|
| corn oil | (linolate, oleate) | 60.6 | 84.6 |
| coconut oil | (palmitate, oleate) | 62.5 | 81.8 |
| rice bran oil | (oleate, linolate) | 62.7 | 89.0 |
| rape-seed oil | (oleate, linolate) | 61.1 | 84.1 |
| olive oil | (oleate) | 62.3 | 81.7 |
| safflower oil | (oleate) | 61.1 | 83.9 |
| kapok oil | (oleate, linolate) | 62.1 | 81.9 |
| sesame oil | (oleate, linolate) | 60.9 | 72.5 |
| cotton-seed oil | (linolate, palmitate) | 62.5 | 85.5 |

(0.5% of the vegetable oil was added to the liquid medium)

EXAMPLE 2

A 500 ml aliquot of an aqueous solution containing 5 g of NH₄NO₃ and 10 g of a fatty acid (as Na salt) shown in Table 4 was sprinkled over 500 g wheat bran. Then each solid medium was put into a 5.0 l Erlenmeyer flask, and heated at 120° C. for 30 minutes for sterilization.

*Aspergillus oryzae* No. 142, grown on potato dextrose agar slants at 30° C. for 3 days was inoculated into the sterilized solid medium and allowed to stand at 31° C. for 3 days.

To this cultured medium, 4.0 l of water was added and the mixture was allowed to stand at 4° C. for 48 hours to extract the enzyme produced. After the extraction process, 3.0 l of aseptic enzyme extract was obtained by filtration of the crude extract through diatomaceous earth on a millipore filter.

The total peptidase activity of each aseptic extract to soybean protein was determined. The results are shown in Table 4.

TABLE 4

Effects of fatty acids on production of the peptidase

| Fatty acid | peptidase activity FN/TN (%) | $G^H$/TN (%) |
|---|---|---|
| none | 50.3 | 47.6 |
| myristic acid | 53.9 | 53.3 |
| palmitic acid | 57.4 | 55.3 |
| stearic acid | 56.8 | 56.4 |
| arachidic acid | 55.1 | 52.9 |
| oleic acid | 53.3 | 51.5 |

EXAMPLE 3

No. 142 strain was cultured in the liquid culture medium shown in Table 1 containing 0.5% vegetable oil and 0.5% of a sugar ester of a fatty acid, as shown in Table 5, in a similar manner as described in Example 1.

The peptidase activity of each culture broth to pure soybean protein was determined and the results are shown in Table 5.

TABLE 5

Effects of vegetable oils used together with sugar esters on production of the peptidase

| vegetable oil | sugar ester | peptidase activity FN/TN (%) | $G^H$/TN (%) |
|---|---|---|---|
| none | none | 56.0 | 60.0 |
| rice bran oil | none | 59.0 | 80.0 |
| " | di, tri palmitate | 63.1 | 89.0 |
| " | monostearate | 62.8 | 92.2 |
| " | di, tristearate | 63.3 | 87.8 |
| " | monopalmitate | 58.0 | 70.0 |
| corn oil | monopalmitate | 62.0 | 83.9 |
| coconut oil | " | 63.1 | 91.3 |
| rape-seed oil | " | 62.4 | 92.3 |
| olive oil | " | 63.2 | 86.5 |
| safflower oil | " | 61.7 | 85.2 |
| kapok oil | " | 62.3 | 88.5 |
| sesame oil | " | 61.9 | 84.1 |
| cotton-seed oil | " | 62.7 | 87.9 |

TABLE 6

Wheat bran extract medium (pH 6.0)

| components | contents (A) | (B) |
|---|---|---|
| wheat bran extract | 10 l | 10 l |
| Ajipron E₂ | 300 g | 300 g |
| KH₂PO₄ | 100 g | 100 g |
| soybean oil | 200 g | — |
| Ryoto sugar ester S-370* | 150 g | — |
| Tap water | 10 l | 10 l |

*sucrose di, tristearate manufactured by Ryoto Co., Inc., Japan

EXAMPLE 4

20 l wheat bran extract medium as shown in column (A) of Table 6 was put into a 30 l jar fermenter, and sterilized at 120° C. for 20 minutes, following which 400 ml of a seed culture broth of *Aspergillus oryzae* No. 142, cultured with shaking in the same manner as described in Example 3, was inoculated, and cultured aerobically at 30° C. for 72 hours with vigorous aeration (1/1 V.V.M.) and stirring at 1,000 r.p.m. (revolutions per minute).

The culture broth was then divided into a 2.0 kg wet microbial beads fraction (containing 75% moisture) and a 17.5 l culture filtrate fraction by an aseptic filtration of the culture broth.

The enzyme activities of these two fractions were determined and the results obtained are shown in Table 7.

TABLE 7

Enzyme activities

| Enzyme activity measured | Activity Test sample | control |
|---|---|---|
| (culture filtrate fraction) | | |
| protease activity at pH 7.0 | 1,600 μ/ml | 400 μ/ml |
| protease activity at pH 9.5 | 1,770 μ/ml | 480 μ/ml |
| (microbial fine beads fraction) | | |
| total peptidase activity | | |
| (FN/TN) | 63% | 56% |
| ($G^H$/TN) | 96% | 53% |
| LAPase activity | 29.0 μ/ml | 8.0 μ/ml |
| glutaminase activity | 55.0 μ/ml | 10.0 μ/ml |

The enzyme activities of the control in Table 7 are those of a culture broth obtained in the same manner except that the liquid culture medium shown in column (B) of Table 6 was used.

The glutaminase activities in Table 7 were determined by the following method:

To 3.0 ml of 10 mM aqueous L-glutamine solution (0.05 M, pH 7.0, phosphate buffer solution was used), 0.2 g of the microbial fine beads which had been broken by glass-homogenizer was added.

The incubation reaction was performed at 37° C. for 4 hours, and stopped by addition of 1 ml of 4% acetic acid solution.

Then, the amount of glutamic acid formed in the clear filtrate of the reaction mixture was determined. 1 unit of the enzyme activity is defined as that enzyme activity which will liberate 1μ mol L-glutamic acid at 37° C. for 60 minutes.

The LAPase activities in Table 7 were determined according to the following method:

To 3.0 ml of 1 mM aqueous leucine paranitroanilide solution (0.05 M, pH 7.0 phosphate buffer solution), 0.2 ml of an enzyme suspension which was prepared by homogenizing the microbial fine beads with a glass homogenizer was added. After being allowed to stand at 37° C. for 10 minutes, the enzyme reaction was stopped by addition of 1.0 ml of 40% acetic acid solution. Then the amount of liberated paranitroaniline in the clear filtrate of the reaction mixture was determined using the usual colorimetric method by measuring the increase of absorbance at 405 mm.

1 unit of the enzyme activity is defined as that enzyme activity which will hydrolyze 1 μM of leucine paranitroanilide at 37° C. for 1 minute. The efficacy of the proteinase preparation was tested. First, 21.0 l of warmed tap water and 23 g solid sodium hydroxide were added to 3.0 kg denatured defatted soybean material. After the mixture had been well stirred, a 570 ml portion of the above clear culture filtrate fraction was added to the mixture, and it was allowed to stand at 45° C. for 5 hours. Then, 18.3 l soybean extract (TN 1.09 g/dl) was obtained by centrifuging the reaction mixture. This extract, after being concentrated to 12 l (TN 1.5 g/dl), was put into a 20 l jar fermenter, and heated at 120° C. for 20 minutes for sterilization.

When the temperature had fallen to about 45° C., a 720 g portion of the microbial fine beads fraction was added to the sterilized substrate and the enzyme reaction was carried out at 45° C. for 5 days in the fermenter with vigorous stirring. Then the hydrolyzate was centrifugated to remove an insoluble residue, to yield 11.7 l of hydrolyzate solution, having TN, FN/TN, $G^H$/TN, and $NH_3$-N/TN of 1.47 g/dl, 68.5%, 110%, and 13.6% respectively. This hydrolyzate solution had a strong, delicious taste and was suitable for use as a raw material for an amino acid seasoning.

Incidentally, the results of a comparison of the hydrolysis ratio among this hydrolyzate solution and commercial premium Yamasa Shoyu (manufactured by Yamasa Shoyu Co., Ltd., Choshi-shi, Japan) and Mieki (commercial chemical soy sauce, manufactured by Ajinomoto Co., Inc.) are shown in Table 8.

TABLE 8

| Comparison of the hydrolysis ratio of amino acid seasonings | | | |
|---|---|---|---|
| amino acid seasoning | hydrolysis ratio | | |
| | FN/TN (%) | $G^H$/TN (%) | $NH_3$—N/TN (%) |
| control* Enzyme-hydrolyzed solution | 52.0 | 56.0 | 13 |
| | 68.5 | 110.0 | 13.6 |
| Yamasa shoyu | 55.5 | 70.5 | — |
| Mieki | 72.0 | 120.0 | — |

*the enzyme-hydrolyzed solution manufactured in the same manner except that medium (B) was used for the enzyme production.

EXAMPLE 5

Both 1.0% Ryoto sugar ester p-1570 and 1.0% purified rice bran oil were added to the basal medium shown in Table 1, and A. oryzae FERM-P 4149 was cultered in the same manner as described in Example 1.

500 ml of the cultured broth thus obtained was then divided into two fractions, a 400 ml clear filtrate fraction and a 100 g microbial fine beads fraction, by aseptic filtration.

40 ml of 5% Ajipron $S_2$ (purified soybean protein containing 85% protein, manufactured by Ajinomoto Co., Inc.) solution (pH 7.0) was put into a 100 ml Erlenmeyer flask and heated at 120° C. for 15 minutes. To this substrate solution, a 10 ml portion of the clear filtrate and a given quantity of the microbial fine beads were added. Then, it was allowed to stand at 40° C. for 5 days and the hydrolysis ratio of the soybean protein was measured.

As a blank test, the same incubation was carried out using sterilized water instead of the Ajipron $S_2$ solution, and the TN and FN of the clear filtrate were determined. These values were subtracted from the test values as blank. The results obtained are shown in FIG. 1. In FIG. 1, the numbers on the abscissa indicate the ratio of dry cell weight (DCW) to concentration of TN of the reaction mixture, and the numbers on the vertical axis are the $G^H$/TN and FN/TN ratios, expressed as percentages.

As shown in FIG. 1, the hydrolysis ratio expressed as FN/TN and $G^H$/TN reaches 72% and 120% when more than 3 DCW/TN of the microbial fine beads is used, and it should be noted that soybean protein can be hydrolyzed by the enzyme process as completely as by an acid hydrolysis process.

EXAMPLE 6

Milk casein (manufactured by Merck & Co., Inc., TN content 14.7%), wheat gluten (manufactured by Ezaki Glico Co., Ltd., Osaka, Japan), and Ajipron $S_2$ were each dissolved in distilled water to prepare 5% solutions (pH 7.0).

40 ml of each of these protein solutions was put into a 100 ml Erlenmeyer flask, and heated at 120° C. for 15 minutes.

Then, 3.4 g of wet (moisture 75%) microbial fine beads produced in the same manner as described in Example 5 was added to these three substrate solutions. The enzymation reaction was carried out at 40° C. for 5 days with occasional stirring. Afterwards, each Erlenmeyer flask and contents was heated at 100° C. for 10 minutes, and a clear filtrate was obtained by filtering each heated reaction mixture with No. 5 B filter paper. The hydrolysis ratio determined for each sample is shown in Table 9, together with results for acid hydrolysis.

TABLE 9

| Comparative hydrolysis ratios of proteins for enzyme process and acid hydrolysis | | | | | |
|---|---|---|---|---|---|
| | | | hydrolysis ratio | | |
| Substrate | | TN (g/dl) | FN/TN (%) | $G^H$/TN (%) | $NH_3$—N/TN (%) |
| milk casein | (E)* | 0.634 | 72.4 | 137 | 8.3 |
| | (A)** | " | (72.0) | 140 | 12.0 |
| wheat gluten | (E) | 0.520 | 71.3 | 232 | 17.5 |
| | (A) | " | (73.2) | 234 | 20.1 |
| Ajipron $S_2$ | (E) | 0.544 | 71.5 | 118 | 12.0 |
| | (A) | " | (72.0) | 120 | 10.9 |

*(E): Enzyme hydrolysis process
**(A): Acid hydrolysis process (hydrolyzed with 6N HCl at 120° C. for 24 hrs.)

It is apparent that the results are quite comparable.

The amino acid compositions of these amino acid solutions were determined by amino acid autoanalyzer (Type KLA 5, manufactured by Hitachi, Ltd., Tokyo). The results obtained are listed in Table 10.

TABLE 10

| | Amino acid composition amino acid (g/dl)/TN (g/dl) × $10^3$ | | | | | |
|---|---|---|---|---|---|---|
| | Ajipron $S_2$ | | milk casein | | wheat gluten | |
| | (E)* | (A)** | (E) | (A) | (E) | (A) |
| Try | 85 | — | 128 | — | 60 | — |
| Lys | 390 | 390 | 524 | 493 | 127 | 112 |
| His | 165 | 165 | 184 | 176 | 117 | 141 |
| Arg | 515 | 510 | 247 | 233 | 230 | 237 |
| Asp | 720 | 740 | 481 | 469 | 232 | 237 |
| Thr | 275 | 260 | 279 | 270 | 169 | 183 |
| Ser | 365 | 325 | 418 | 368 | 306 | 340 |
| Glu | 1,190 | 1,200 | 1,367 | 1,400 | 2,219 | 2,340 |
| Pro | 315 | 385 | 722 | 735 | 760 | 930 |
| Gly | 245 | 270 | 127 | 152 | 190 | 237 |
| Ala | 330 | 298 | 218 | 184 | 188 | 189 |
| Cys | 40 | 40 | 15 | 16 | 68 | 131 |
| Val | 345 | 305 | 420 | 421 | 278 | 289 |
| Met | 103 | 22 | 195 | 183 | 123 | 117 |
| Ileu | 328 | 245 | 371 | 375 | 238 | 264 |
| Leu | 520 | 477 | 623 | 597 | 423 | 289 |
| Tyr | 180 | 185 | 117 | 230 | 199 | 237 |
| Phe | 3.0 | 320 | 226 | 311 | 306 | 361 |

*Enzyme process
**Acid-catalyzed hydrolysis process

Having now fully described the invention, it will be apparent to one of ordinary skill in the art that many changes and modifications can be made thereto without departing from the spirit or scope of the invention as set forth herein.

What is claimed as new and intended to be coverd by letters Patent is:

1. A method for producing a peptidase capable of substantially completely hydrolyzing protein into its constituent amino acids which comprises culturing a strain of filamentous fungus, belonging to one of the species *Aspergillus oryzae* and *Aspergillus sojae* and characterized in that said strain is capable of producing said peptidase, in a nutrient culture medium containing
   (a) a protein selected from the group consisting of soybean protein, defatted soybean, wheat, wheat bran, wheat bran extract, and mixtures thereof, and
   (b) at least one substrate selected from the group consisting of a fatty acid having 14, 16, 18 or 20 carbon atoms and a derivative of said fatty acid,
and recovering said peptidase from said culture medium.

2. The method of claim 1, wherein said fatty acid is myristic, palmitic, stearic, oleic, linoleic, and arachidic acid.

3. The method of claim 1, wherein said derivative of said fatty acid is at least one member selected from the group consisting of a sugar ester, a sorbitan ester, a polyoxyethylene sorbitan ester, and a glycerine ester of said fatty acid, a phospholipid, and a vegetable oil containing said fatty acid.

4. The method of claim 3, wherein said vegetable oil is soybean, corn, coconut, rice, rape-seed, olive, kapok, sesame, cotton-seed, safflower oil, or mixtures thereof.

5. The method of claim 3, wherein said phospholipid is phosphatidyl ethanolamine, phosphatidyl choline, lecithin, or mixtures thereof.

6. The method of claim 3, wherein said nutrient culture medium is a nutrient liquid culture medium containing said sugar ester so that the microbial cells of said fungus form microbial fine beads.

7. The method of claim 3, wherein said nutrient culture medium is a nutrient liquid culture medium containing both said vegetable oil and said sugar ester of said fatty acid.

8. The method of claim 7, wherein said nutrient liquid medium contains 0.5 to 4.0% of a mixture of wheat bran and defatted soybean.

9. The method of claim 6, wherein said fungus is aerobically cultured in said nutrient liquid culture medium at a temperature of from 20° to 40° C. at a pH of from 3.5 to 8.5 for from 2 to 10 days.

* * * * *